United States Patent [19]

Obermann et al.

[11] Patent Number: 4,985,015
[45] Date of Patent: Jan. 15, 1991

[54] DOSING DEVICE FOR CONTROLLED INJECTION OF LIQUID FROM A RESERVOIR INTO AN ORGANISM

[75] Inventors: Peter Obermann, Erlangen; Manfred Franetzki, Uttenreuth, both of Fed. Rep. of Germany

[73] Assignee: Siemens Aktiengesellschaft, Berlin and Munich, Fed. Rep. of Germany

[21] Appl. No.: 275,366

[22] Filed: Nov. 23, 1988

[30] Foreign Application Priority Data

Nov. 25, 1987 [DE] Fed. Rep. of Germany ....... 3739972
Jul. 20, 1988 [EP] European Pat. Off. ........... 88111725

[51] Int. Cl.$^5$ .............................................. A61M 5/20
[52] U.S. Cl. .................................... 604/67; 604/152
[58] Field of Search ............... 604/65, 66, 67, 151, 604/152; 600/12, 13

[56] References Cited

U.S. PATENT DOCUMENTS

| | | | |
|---|---|---|---|
| 4,024,864 | 5/1977 | Davies et al. ................... 604/154 X |
| 4,209,014 | 6/1980 | Sefton ................................ 604/152 |
| 4,395,259 | 7/1983 | Prestele et al. . | |
| 4,486,190 | 12/1984 | Reinicke ............................. 604/67 |
| 4,494,950 | 1/1985 | Fischell .............................. 604/66 |
| 4,561,443 | 12/1985 | Hogrefe et al. ..................... 604/65 |
| 4,808,089 | 2/1989 | Buchholtz et al. ................ 604/152 |
| 4,871,351 | 10/1989 | Feingold ............................. 604/66 |

FOREIGN PATENT DOCUMENTS 378123  6/1985 Austria .
2916490 11/1980 Fed. Rep. of Germany .

*Primary Examiner*—C. Fred Rosenbaum
*Assistant Examiner*—Corrine Maglione
*Attorney, Agent, or Firm*—Hill, Van Santen, Steadman & Simpson

[57] ABSTRACT

A dosing device of the type which can be implanted in a patient to control injection of liquids from a reservoir into the patient has an electrically controllable piston pump and a circuit responsible for controlling and monitoring the operation of the pump. The circuit includes a unit for acquiring a chronological curve representative of the piston motion, and electrical signals proportional thereto are obtained. These signals are supplied to control elements which compare these signals to prescribed rated values, and generate control and alarm signals given deviations of the incoming signals from the rated values.

21 Claims, 4 Drawing Sheets

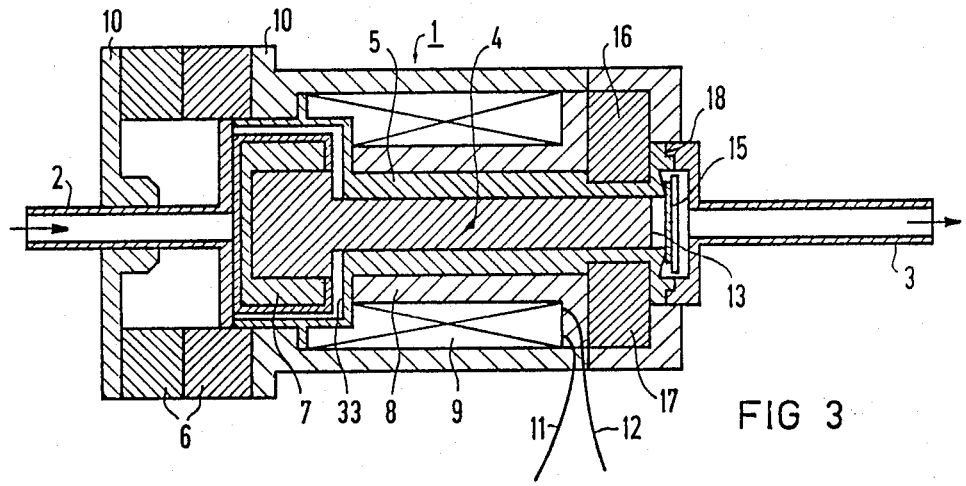
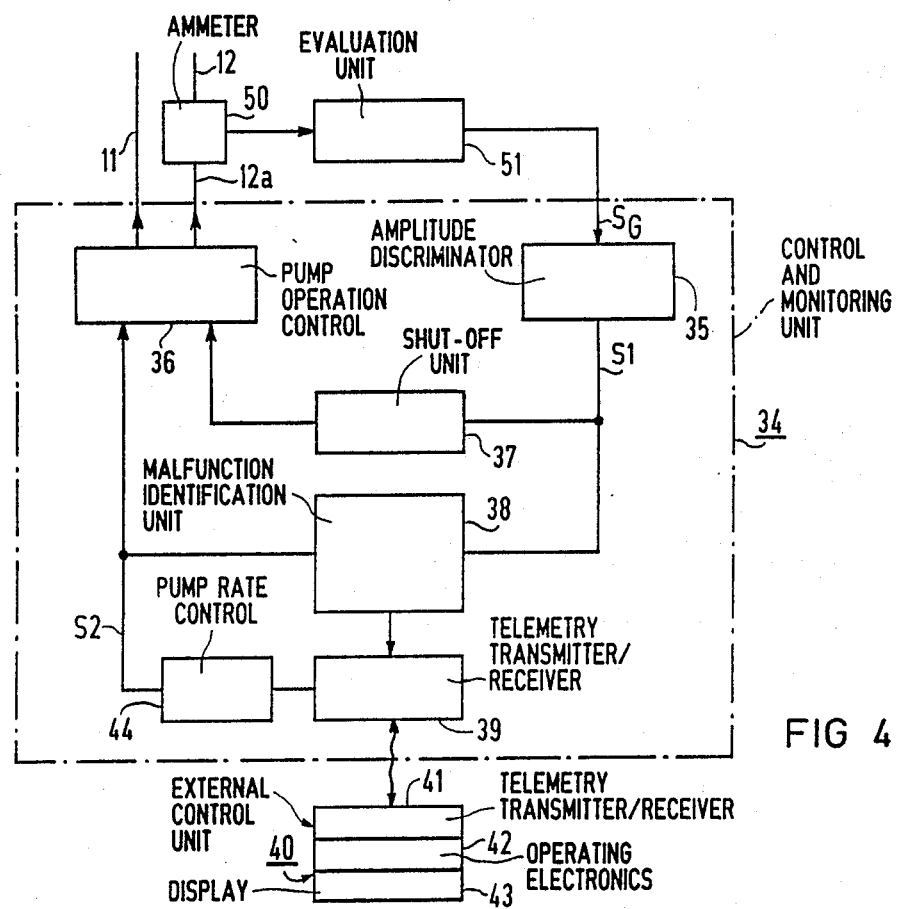

DOSING DEVICE FOR CONTROLLED INJECTION OF LIQUID FROM A RESERVOIR INTO AN ORGANISM

BACKGROUND OF THE INVENTION

1. Field of the Invention

The present invention is related to implantable medication dosing devices, and, in particular, to such a dosing device which permits controlled injection of liquid from a reservoir into a patient.

2. Description of the Prior Art and Related Applications

Implantable dosing devices are known for use in diabetes therapy which inject insulin from a reservoir into the body in accordance with a defined dosing program. The pump portion of such devices is preferably implanted, and the operating or programming part is extracorporeally disposed. Communication between the implanted and the extracorporeally units ensues by telemetric remote control. Because the pump of the dosing device is a part of the implanted unit, an energy source for the pump in the form of a battery must also be implanted. To achieve an optimally long service life of the battery, an efficient energy utilization by the pump drive is of special significance. It is also important to monitor the quantity of liquid conveyed and injected by the pump because life-threatening conditions could otherwise occur.

U.S. Pat. No. 4,486,190 discloses a dosing device of the type described above wherein the pump operation is monitored by a flow resistor at the pump output, and a pressure sensor in the pump chamber. This embodiment is suitable for diaphragm pumps, and is somewhat technologically complicated. This device is not suitable for piston pumps because piston pumps operate based on an optimized relationship between piston capacity and dead space, and are capable of pumping gases with a relatively high conveying rate given differential pressures, which cannot be suitably monitored by the above structure.

Moreover, such piston pumps can still convey the liquid to be injected even though gas bubbles may be situated in the liquid. In fact, the presence of such gas bubbles in piston pumps is substantially unavoidable in practice. Such a piston pump is disclosed in European application No. 87112040.8, and in copending U. S. application Ser. No. 182,723 (Franetzki et al) filed Apr. 18, 1988 now U.S. Pat. No. 4,883,467. In the pump of the latter application, structure has been disclosed to minimize formation and conveyance of such bubbles.

A further monitoring arrangement for an implantable piston pump in a medication dosing device is described in Austrian Patent No. 378 123. In the structure described therein, the noise generated by the normal operation of the drive coils of the piston of the piston pump is monitored by a noise sensor (microphone), and an alarm signal is triggered in the absence of such noise. It is not possible in this system to monitor the pump for functional deviations from rated values or to provide control instructions in the event of such deviations.

Another monitoring arrangement for an implanted infusion pump of a medication dosing device is described in European application No. 0 048 423. In this structure, electrically operating pulses ar wirelessly supplied to the pump drive, and an answerback is provided also wirelessly, to an externally disposed control unit or programming device and the reception of these pulses is confirmed. It is not possible in this system, however, to confirm whether the transmitted pulses have actually resulted in a pump motion which conveys the desired quantity of medication.

Another pump monitoring device in a pump for compressing ethylene gas is described in German No. OS 2 916 490, In this monitoring system, the function of the valves is monitored by obtaining, with an oscillatory pick-up, sound waves transmitted by the pump operation to the cylinder head, and comparing the signals received in this manner to rated values. An alarm or shut-off signal is triggered given recognition of a malfunction.

SUMMARY OF THE INVENTION

It is an object of the present invention to provide a dosing device for controlled injection of liquid medication from a reservoir into an organism wherein the pump function can be monitored with simple electrical or mechanical means, and time-dependent curves generated from the monitoring, which are then used to conduct an analysis of the operation of the pump, with appropriate control or display signals being thereby obtained.

The above object is achieved in accordance with the principles of the present invention in a dosing device including means for obtaining measurements representative of a chronological curve of the motion of the piston. The signals corresponding to this curve are supplied to and therefore amplitude descriminator. The output of this unit is supplied to a shut-off unit which supplies a control signal ceasing operation of the pump under certain conditions, as well as to a malfunction identification unit which identifies one of several possible types of malfunctions, and initiates the generation of suitable control signals to correct such malfunctions.

The start and end of the piston stroke of the pump can be unambiguously identified in this system, and the energy feed to the stator winding which operates the movement of the piston can be optimally controlled. Additionally, by analysis of the motion curve of the piston, information related thereto can be communicated via telemetry link to an external programming-/control unit, which may also be equipped with a display and an alarm system, so that significant deviations from rated values can be immediately identified.

A noise sensor may be used to acquire the signals which are then used to construct the time-dependent motion curve of the piston, or the electrically feed to the drive for the piston can be directly monitored to obtain such signals.

BRIEF DESCRIPTION OF THE DRAWINGS

FIG. 3 is a side sectional view of a further embodiment of a pump for a dosing device constructed in accordance with the principles of the present invention.

FIG. 4 is a block circuit diagram of an implanted control and monitoring unit for the pump shown in FIG. 3, together with an external control unit.

DESCRIPTION OF THE PREFERRED EMBODIMENTS

Figure 1:
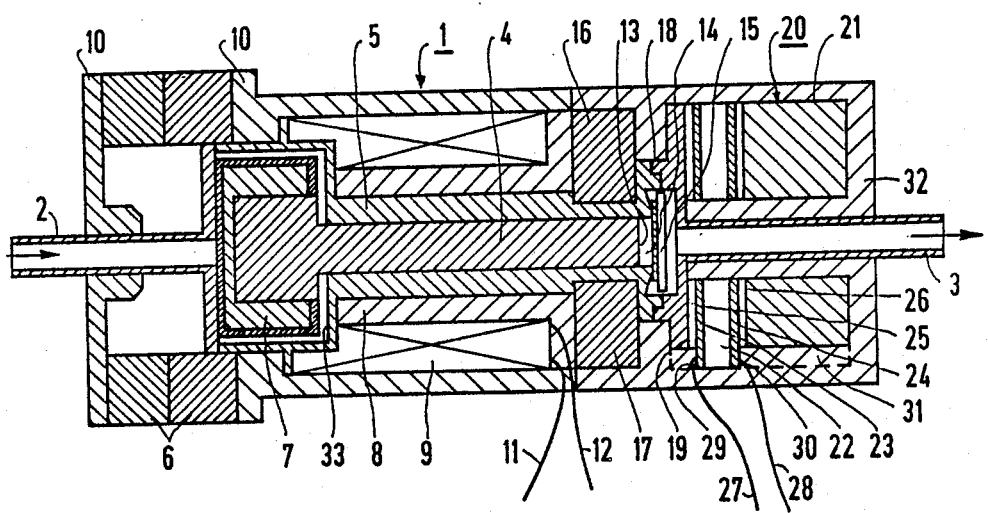
FIG. 1 is a side sectional view of a pump for a dosing device constructed in accordance with the principles of the present invention.

A first embodiment of a piston pump 1 of a medication dosing device constructed in accordance with the principles of the present invention is shown in section in FIG. 1. The piston pump 1 includes a medication input 2 and a medication output of discharge 3 for a liquid medication, such as insulin, to be injected into an organism. The piston pump 1 further includes a piston 4 contained within a cylinder housing 5. A piston drive system includes permanent magnets 6, an encapsulated armature 7 and a stator 8 with a stator winding 9. The respective pole shoes of the permanent magnets 6 and the stator 8 are referenced 10. The stator winding is connected by leads 11 and 12 to an energy source (not shown) and to a control and monitoring unit 34 (shown in FIG. 2 and discussed in detail below) and an end face 13 of the piston 4 limits a chamber 14 (which defines the piston capacity) formed by the surrounding portion of the cylinder housing 5 and a valve 15. Given the occurrence of a driving force by exciting the stator winding 9, the piston 4 moves in a direction toward the valve 15, and its end face 13 thereby expresses the liquid medication situated in the chamber 14 through the valve 15 into the output 13 against the restoring force of further permanent magnets 16 and 17. The medication proceeds from the output 3 to a catheter (not shown) having a tip with an injection cannula introduced into a body vessel, so that the medication is injected into this vessel.

After the end face 13 of the piston 4 strikes the inner valve wall, when no liquid pressure remains, the valve 15 closes due to the restoring force exerted by the permanent magnet 16 and 17. A noise sensor 20 is disposed concentrically relative to the output 3 at an outlet side of a flange 19 of the piston pump 1. The noise sensor 20 consists of a piezoceramic ring disc 22 connected by a metallic coupling mass 21, which serves as a references mass and may consist of, for example, brass or steel. Two metal layers 23 and 24 serve as electrodes. Each layer 23 and 24 has a respective insulating layers 25 or 26 consisting of epoxy resin. The two insulating layer 25 and 26 simultaneously serve as adhesive for fastening the noise sensor 20 to the flange 19, and for fastening the coupling mass 21 to the piezoceramic ring disc 22.

The metal layers 23 and 24 are connected at respective points 29 and 30 to output lines 27 and 28, which are conducted toward the interior of the piston pump 1 in recesses 31 of the flange 19 and the coupling mass 21.

For mechanical stabilization, the noise sensor 20 is arranged in a housing 32 of epoxy resin casting compound, which is fixed to the remainder of the piston pump 1.

The armature 7, which is rigidly connected to the piston 4, is disposed so that an annular face thereof at the output side lies against an annular surface 33 of the cylinder housing 5 at the input side. When these two surfaces strike each other, a stop noise is generated, which can be distinguished from therefore; and the general pump noise. This stop noise is acoustically transmitted to the noise sensor 20 by the cylinder housing 5 and the flange 19. This acoustic stop noise is sensed by the noise sensor 20, and is converted into a electrical output signal $S_G$, which is supplied along lines 27 and 28.

Figure 2:
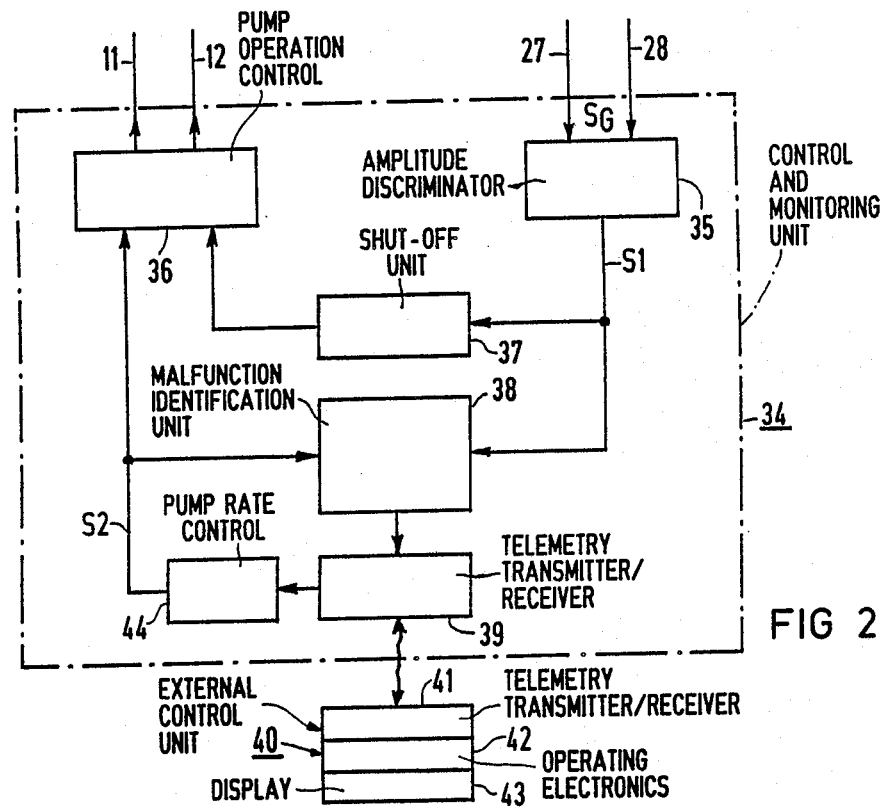
FIG. 2 is a block circuit diagram of an implanted control and monitoring unit for the pump shown in FIG. 1, together with an external control unit.

A basic circuit diagram of a control and monitoring unit 34 for the pump shown in FIG. 1 is shown in FIG. 2. The unit 34 processes the output signal $S_G$ of the noise sensor 20 so that the stop noise, contained within this signal, can be used for both controlling and for monitoring the piston pump 1.

To that end the output lines 27 and 28 of the noise sensor 20 are connected to the input of an amplitude discriminator 35. Drive lines 11 and 12 of the stator winding 9 are connected to the output of a pump operation control 36. The amplitude discriminator 35 (which may be a threshold discriminator) has an output connected to the respective input of a shut-off unit 37 and a malfunction identification unit 38. The malfunction identification unit 38 has an output connected to a telemetry transmitter/receiver 39. The transmitter/receiver 39 is in communication via telemetry link with an external control unit (programming unit) 40. The telemetry transmitter/receiver 39 has an output connected to the input of a pump rate control 44, which generates an output signal $S_2$ proceeding to a further input of the malfunction identification unit 38, as well as to the input of the pump operation control 36. A further input of the pump operation control 36 is connected to an output of the shut-off unit 37.

The external control unit 40 includes a telemetry transmitter/receiver, operating electronics generally referenced 42, and a display 43 for generating an optical, acoustic or tactile (i.e., a subcutaneous stimulation current) alarm display or signal. The pump rate control 44 is programmable by the external control unit 40 using the operating electronics 42, with the instructions being entered via operating electronics 42 being transmitted to the implanted unit 34 via telemetry link.

Known electrical pump noises are generated during each pump cycle, and are contained within the signal $S_G$, with the stop noises caused by the armature 7 coming into contact with the end face 33 of the cylinder housing 5 being identifiable over these normal pump noises within the signal $S_G$. When such a signal occurs corresponding to a stop noise the amplitude discriminator 35 generates a corresponding output signal $S_1$. This signal $S_1$ is supplied to the shut-off unit 37, which in turn generates a corresponding control signal which is supplied to the pump operational electronics 36, and causes interruption of the circuit of the stator winding 9 until a new turn-on signal has been produced by the pump rate control 44 in accord with the program. Consequently, the piston pump 1 is always shut-off at the end of a pump action. Thus it is not necessary, as in conventional devices, to wait for the transmittal of an answerback signal which necessarily requires a finite time during which the pump is still operating (perhaps unnecessarily, and thereby consuming unnecessary power) or during which he pump is operating in a malfunctioning manner.

The output signal $S_1$ from the amplitude discriminator 35, supplied to the malfunction identification unit 38, is analyzed in the unit 38 as representative of the chronological course of the motion of the piston, and is analyzed in the malfunction identification unit 38 for deviations from typical piston courses in view of amplitude and time. For example, it can be determined in the unit 38 whether the pump may be blocked, whether the pump is conveying gas bubbles, whether no liquid is being conveyed due to an empty medication reservoir, or whether an incipient catheter plugging is present. To that end, the output signal $S_2$ of the pump rate control 44 is chronologically correlated with the output signal $S_1$ of the amplitude discriminator 35 in the malfunction identification unit 38. A different output signal status respectively occurs in the cases of different types of signal deviations due to different types of malfunctions. For example, given a blockage of the catheter, no output signal $S_1$ occurs at all during the correlation time interval. If the medication reservoir is empty, the output signal $S_1$ will be greatly premature relative to the signal $S_2$. If bubbles are being conveyed in the liquid, the signal $S_1$ will be slightly premature relative to the signal $S_2$. If catheter blockage is beginning occur, the signals $S_1$ will still be received, however, due to the increasing catheter flow resists given a low pumping rate (base rate), these signals $S_1$ will disappear when a switch to high pumping rates is undertaken.

The nature of the malfunction is communicated from the malfunction identification unit 33, via a telemetry link., for example, at the next programming event, to the display 43 of the external control unit 40 and is optically, acoustically and/or tacitly indicated. This information, which may be possibly coupled with an alarm signal, enables the wearer of the dosing device to initiate suitable therapeutic measures, or measures to eliminate the malfunction, at an early time.

Figure 6:
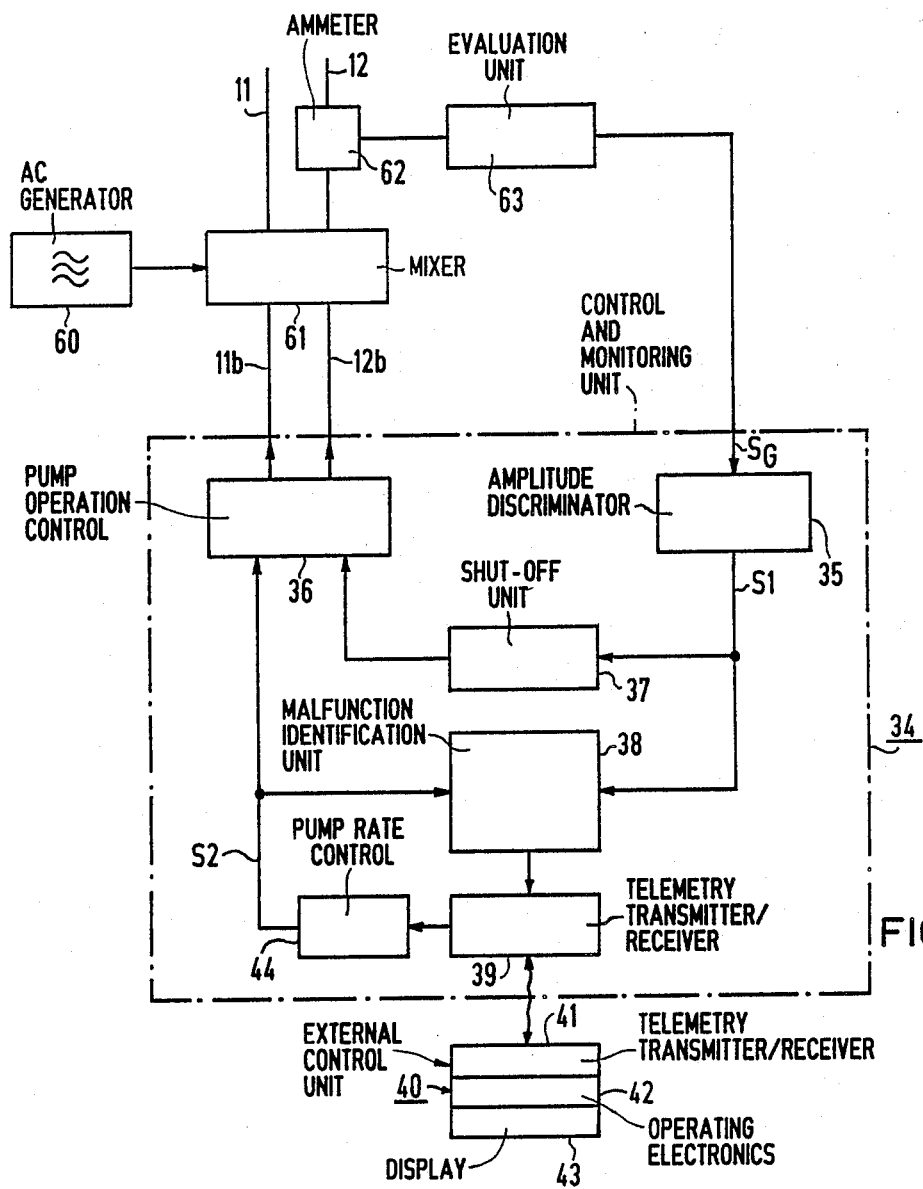
FIG. 6 is a block circuit diagram of a further embodiment of an implanted control and monitoring unit for the pump shown in FIG. 3, together with an external control unit.

Another embodiment of a piston pump a is shown in FIG. 3, and two embodiments of control and monitoring circuitry therefore are respectively shown in FIGS. 4 and 6. In the embodiment of FIG. 3, components identical to those shown in FIG. 1 are identified with the same reference numerals. In the embodiment of FIG. 3, the noise sensor, used in the embodiment of FIG. 1, is eliminated in favor of purely electrical monitoring of the stator winding 9. As shown in FIG. 3, the piston pump a is shorter than the pump 1 in the embodiment of FIG. 1, which is of particular importance for implanted pumps. In the embodiment of FIG. 3, however, only the point in time at which the piston strikes the end wall 33 of the cylinder wall 5 can be monitored as well as monitoring the deration and the speed of the pump motion. Monitoring these quantities, however, permits the operation of the pump to be controlled in a manner sufficient for most uses.

In the circuitry embodiment shown in FIG. 4, the control and monitoring unit 34 itself is identical to that already described in connection with FIG. 2. In the embodiment of FIG. 4, however, the input signal $S_G$ to the amplitude discriminator 35 is not derived from a noise sensor, but rather from the circuit of the stator winding 9. For this purpose, an ammeter 50 is interconnected in the lead 12 of the stator winding circuit, and an output signal proportional to current to the winding circuit is conducted from the ammeter 50 to an evaluation unit 51. The output signal of the ammeter 50 is differentiated in the evaluation unit 51, and the differentiated signal is supplied to the input of the amplitude discriminator 35.

Figure 5:
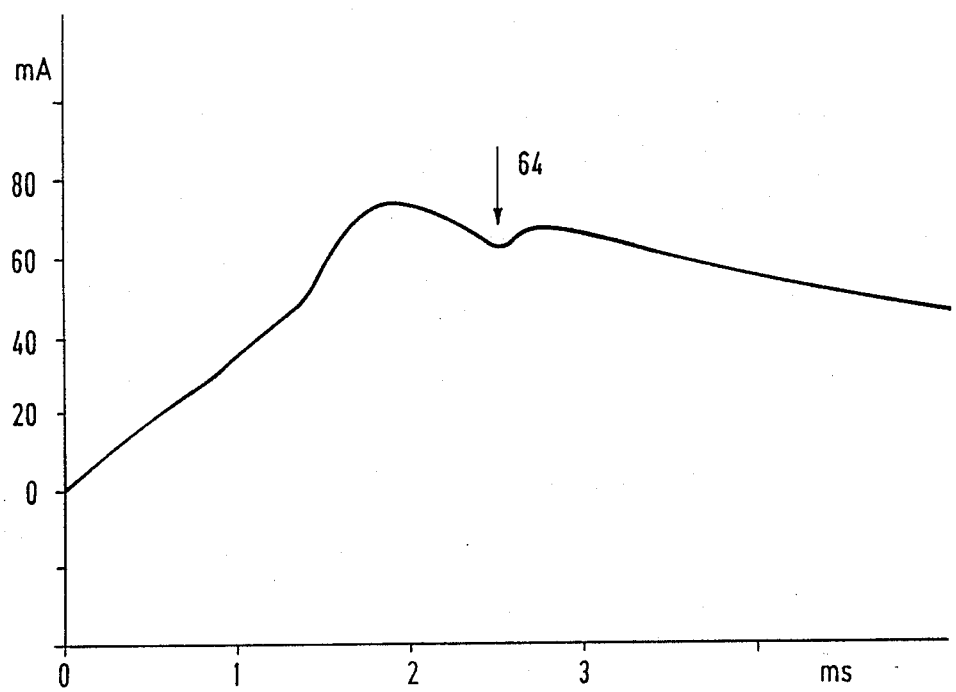
FIG. 5 is an example of a time-dependent curve representative of the piston derived from current flowing through the stator winding.

FIG. 5 shows the curve of the current through the stator winding 9, dependent on time, given normal function of the pump 1a. The location indicated by the arrow 64 identifies the stop of the piston. As can been see, this results in a noticeable fade or decrease of the current, which can be easily acquired by differentiating the signal corresponding to the current. This occurs in the evaluation unit 51, and results in a signal $S_G$ which can be further processed in the control and monitoring circuit 34 in the manner already described above. In a further circuitry embodiment shown in FIG. 6, the inductance of the stator winding 9 is measured, instead of the current. For this purpose, an ac voltage produced by a generator 60 is combined in a mixer 61 with the excitation dc voltage, and the combination (the output of the mixer 61) is supplied by lines 11 and 12 to the stator winding, so that the normal excitation dc voltage has the ac voltage superimposed thereon. The amplitude of the ac current flowing through the stator winding 9 is dependent on the inductance of the stator winding. This ac current is measured in an ammeter 62. The inductance of the stator winding 9 changes due to the motion of the piston 4 due to the change of the magnetic flux in its magnetic circuit. After the stop, by contrast, the inductance of the winding remains constant. The point in time at which the output of the ammeter 62 becomes constant can be determined by differentiating the rectified ac signal. This takes place in an evaluation unit 63, which generates an output signal $S_G$ supplied to the input of the amplitude discriminator 35. This signal $S_G$ is again processed in the control and monitoring unit 34 as already described.

Although modifications and changes may be suggested by those skilled in the art it is the intention of the inventors to embody within the patent warranted hereon all changes and modifications as reasonably and properly come within the scope of their contribution to the art.

We claim:

1. A dosing device for injecting liquids from a reservoir into an organism comprising:
   pump means for transferring said liquid said reservoir to said organism in a selected dose, said pump means including a cylinder housing with a movable piston disposed in said cylinder housing, said pump means further including energizable electromagnetic excitation means for moving, if energized, said piston from a rest position in said cylinder housing through a stroke to convey said liquid through said pump means to said organism, and restoring means for returning said piston to said rest position when the electromagnetic excitation means is not energized;
   noise sensor means arranged relative to said pump means for obtaining a signal representing a time-dependent curve of the piston motion for each stroke;
   means connected to said noise sensor means for monitoring the amplitude of said curve; and
   means in communication with said means for monitoring the amplitude of said curve for generating a corrective signal, if needed, based on said amplitude of said curve.

2. A dosing device as claimed in claim 1, further comprising means, connected to said means for monitoring and in communication with said means for generating a corrective signal, for identifying a specific malfunction in the operation of said pump means based on said amplitude of said curve.

3. A dosing device as claimed in claim 2, wherein said means for identifying malfunctions includes means for monitoring the duration of each stroke.

4. A dosing device as claimed in claim 2, wherein said means for identifying malfunctions includes means for comparing said curve to a selected rated curve.

5. A dosing device as claimed in claim 1, wherein said means for generating a corrective signal includes means for generating a control signal to said electromagnetic excitation means to alter the operation of the said pump means.

6. A dosing device as claimed in claim 1, wherein said means for generating a corrective signal includes means for generating an alarm signal.

7. A dosing device as claimed in claim 1, further comprising means connected to said electromagnetic excitation means for periodically energizing it to move said piston through successive strokes, and wherein said cylinder housing has a cylinder wall against which said piston strikes at the end of each stroke thereby generating a distinctive amplitude in said time-dependent curve of the piston motion, and wherein said dosing device further comprises shut-off means connected to said means for monitoring the amplitude of said curve for de-energizing said electromagnetic excitation means upon the occurrence of said distinctive amplitude until a next energizing of said electromagnetic excitation means by said means for energizing.

8. A dosing device as claimed in claim 1, wherein said pump means, said means for obtaining a signal and said means for monitoring are implanted in said organism, and wherein said means for generating a corrective signal is extracorporally disposed relative to said organism, and further comprising implanted means, connected to said means for monitoring the amplitude, for transmitting and receiving telemetry signals to and from said means for generating a corrective signal, and wherein said means for generating a corrective signal includes means for transmitting and receiving telemetry signals from said implanted means for transmitting and receiving.

9. A dosing device as claimed in claim 8, wherein said means for generating a corrective signal further includes means for displaying a signal transmitted by telemetry corresponding to said corrective signal.

10. A dosing device as claimed in claim 8, wherein said means for generating a corrective signal further comprises programming means for manually entering said corrective signal for telemetry transmission to said pump means via implanted means for transmitting and receiving telemetry signals.

11. A dosing device as claimed in claim 1, wherein said pump means includes a liquid discharge channel, and wherein said noise sensor is disposed concentrically relative to said discharge channel.

12. A dosing device as claimed in claim 1, wherein said noise sensor comprises a piezoceramic element having electrodes and a coupling mass connected thereto, said electrodes being connected to said means for monitoring the amplitude of said curve.

13. A dosing device as claimed in claim 12, wherein said cylinder housing has an interior end face disposed substantially at a termination of a stroke of said piston, and wherein said piezoceramic element is a ring disc disposed against said end face and held against said end face with a flange.

14. A dosing device as claimed in claim 1, wherein each of said piston strokes, includes an intake event wherein said liquid is drawn from said reservoir and an ejection event wherein liquid is discharged from said pump means into said organism, each of said intake event and said ejection event generating noises within a respective frequency range, and wherein said noise sensor consists of piezoceramic material sensitive to said respective frequency ranges.

15. A dosing device for injecting liquids from a reservoir into an organism comprising:
   pump means for transferring said liquid from reservoir to said organism in a selected dose, said pump means including a cylinder housing with a movable piston disposed in said cylinder housing, said pump means further including, electromagnetic excitation means connected to means for energizing for moving, if energized, said piston from a rest position in said cylinder housing through a stroke, to convey said liquid through said pump means to said organism, and restoring means for returning said piston to said rest position when the electromagnetic excitation means is not energized;
   means arranged relative to said pump mens for obtaining a signal representing a time-dependent curve of the piston motion for each stroke;
   means connected to said means for obtaining a signal for monitoring the amplitude of said curve;
   said cylinder housing having a wall against which said piston strikes at an end of each stroke thereby generating a distinctive amplitude in said time-dependent curve;
   shut-off means connected to said means for monitoring and to said means for energizing for disconnecting said means for energizing upon the occurrence of said distinctive amplitude in said time-dependent curve until the next energization of said electromagnetic excitation means by said means for energizing; and
   means connected to said means for monitoring for identifying specific malfunction in the operation of said pump means based on said amplitude and for generating a control signal to alter the operation of said pump means to correct said malfunction.

16. A dosing device as claimed in claim 15, wherein said means for obtaining signal representing a time-dependent of the curve of the piston motion is a means for sensing noise generated by movement of said piston in said cylinder housing.

17. A dosing device as claimed in claim 15, wherein said electromagnetic excitation means includes a stator winding, and wherein said means for obtaining signals representing a time-dependent curve of the piston motion for each stroke is a means for measuring a current through said stator winding.

18. A dosing device for injecting liquids from a reservoir into an organism comprising:
   pump means for transferring said liquid from said reservoir to said organism in a selected dose, said pump means including a cylinder housing with a movable piston disposed in said cylinder housing, said pump means further including energizable electromagnetic excitation means including a stator winding for moving, if energized, said piston from a rest position in said cylinder housing through a stroke to convey said liquid through said pump means to said organism, and restoring means for returning said piston to said rest position when the electromagnetic excitation means is not energized;
   means arranged relative to said pump means for obtaining a signal representing a time-dependent curve of the piston motion for each stroke, including means connected to said stator winding for superimposing an a.c. signal on a d.c. energizing signal in said stator winding, an ammeter connected to said stator winding for measuring the a.c. signal after the signal has passed through said stator winding, and evaluation means connected to an output of said ammeter for differentiating the output signal of said ammeter;

means connected to the output of said evaluation means for monitoring the amplitude of said curve; and means in communication with said means for monitoring the amplitude of said curve for generating a corrective signal, if needed, based on said amplitude of said curve.

19. A dosing device as claimed in claim 18, further comprising means connected to said electromagnetic excitation means for periodically energizing it to move said piston through successive strokes, and wherein said cylinder housing has a cylinder wall against which said piston strikes at the end of each stroke thereby generating a distinctive amplitude in said time-dependent curve of the piston motion, and wherein said dosing device further comprises shut-off means connected to said means for monitoring the amplitude of said curve for de-energizing said electromagnetic excitation means upon the occurrence of said distinctive amplitude until a next energization of said electromagnetic excitation means by said means for energizing.

20. A dosing device for injecting liquids from a reservoir in to an organism comprising:

pump means for transferring said liquid from said reservoir to said organism in a selected dose, said pump means including a cylinder housing with a movable piston disposed in said cylinder housing, said pump means further including energizable electromagnetic excitation means including a stator winding for moving, if energized, said piston from a rest position in said cylinder housing through a stroke to convey said liquid through said pump means to said organism and restoring means for returning said piston to said rest position when the electromagnetic excitation means is not energized;

means arranged relative to said pump means for obtaining a signal representing a time-dependent curve of the piston motion for each stroke, including an ammeter connected to said stator winding, and an evaluation means having an input connected to an output of said ammeter for differentiating the output signal of said ammeter;

means connected to an output of said evaluation means for monitoring the amplitude of said curve; and means in communication with said means for monitoring the amplitude of said curve for generating a corrective signal, if needed, based on said amplitude of said curve.

21. A dosing device as claimed in claim 20, further comprising means connected to said electromagnetic excitation means for periodically energizing it to move said piston through successive strokes, and wherein said cylinder housing has a cylinder wall against which said piston strikes at the end of each stroke thereby generating a distinctive amplitude in said time-dependent curve of the piston motion, and wherein said dosing device further comprises shut-off means connected to said means for monitoring the amplitude of said curve for de-energizing said electromagnetic excitation means upon the occurrence of said distinctive amplitude until a next energization of said electromagnetic excitation means by said means for energizing.

* * * * *